US011110290B2

(12) United States Patent
Tischendorf et al.

(10) Patent No.: US 11,110,290 B2
(45) Date of Patent: Sep. 7, 2021

(54) IMPLANTABLE DEVICE WITH OPTICAL LEAD

(71) Applicant: Medtronic, Inc., Minneapolis, MN (US)

(72) Inventors: Brad C. Tischendorf, Minneapolis, MN (US); Gordon O. Munns, Stacy, MN (US); Christian S. Nielsen, River Falls, WI (US); John D. Norton, St. Paul, MN (US); Markus W. Reiterer, Plymouth, MN (US); Andrew J. Thom, Maple Grove, MN (US); Kunal J. Paralikar, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 81 days.

(21) Appl. No.: 16/291,170

(22) Filed: Mar. 4, 2019

(65) Prior Publication Data
US 2019/0201709 A1    Jul. 4, 2019

Related U.S. Application Data

(62) Division of application No. 14/694,134, filed on Apr. 23, 2015, now Pat. No. 10,245,441.
(Continued)

(51) Int. Cl.
*A61N 5/06* (2006.01)
*A61N 1/05* (2006.01)

(52) U.S. Cl.
CPC ............. *A61N 5/0601* (2013.01); *A61N 1/05* (2013.01); *A61N 2005/0626* (2013.01); *A61N 2005/0651* (2013.01)

(58) Field of Classification Search
CPC ...... A61N 5/06; A61N 5/0601; A61N 5/0613; A61N 5/0622; A61N 2005/063; A61N 2005/0632; A61N 2005/0643; A61N 2005/065; A61N 2005/0651; A61N 2005/0652; A61N 2005/067; A61N 1/36;
(Continued)

(56) References Cited

U.S. PATENT DOCUMENTS 5,445,608 A *  8/1995  Chen ................... A61N 5/0601
                                                          604/19
5,556,421 A     9/1996  Prutchi et al.
(Continued)

FOREIGN PATENT DOCUMENTS

WO    WO 2008/105691 A1    9/2008

OTHER PUBLICATIONS

U.S. Appl. No. 60/865,763, filed Nov. 14, 2006, Thom et al.
(Continued)

*Primary Examiner* — Ahmed M Farah
(74) *Attorney, Agent, or Firm* — Mueting Raasch Group

(57) ABSTRACT

An implantable active medical device system includes an active medical device and a lead extending between a proximal portion electrically coupled to the active medical device and a distal end portion configured to emit light. The distal end portion includes a solid state light source disposed within a light transmissive ring element. The light transmissive ring element forms an exterior segment of the distal end portion. The light transmissive ring element defines at least a portion of a hermetic cavity.

17 Claims, 4 Drawing Sheets

Related U.S. Application Data

(60) Provisional application No. 61/984,341, filed on Apr. 25, 2014.

(58) Field of Classification Search
CPC .............. A61N 1/3605; A61N 1/36053; A61N 1/36057; A61N 1/3606; A61N 1/36062; A61N 1/36064; A61N 1/36067; A61N 1/36071; A61N 1/36075
USPC ................................................ 607/88–90, 92
See application file for complete search history.

(56) References Cited

U.S. PATENT DOCUMENTS

| | | | |
|---|---|---|---|
| 5,902,236 | A | 5/1999 | Iverson |
| 6,198,952 | B1 | 3/2001 | Miesel |
| 7,349,618 | B2 | 3/2008 | Nielsen et al. |
| 7,519,261 | B2 | 4/2009 | Nielsen et al. |
| 7,711,428 | B2 | 5/2010 | Janzig |
| 8,192,418 | B2 | 6/2012 | Robinson et al. |
| 8,288,654 | B2 | 10/2012 | Taylor et al. |
| 8,396,570 | B2 | 3/2013 | Dadd et al. |
| 8,538,530 | B1 | 9/2013 | Orinski |
| 8,936,630 | B2 | 1/2015 | Denison et al. |
| 10,245,441 | B2 * | 4/2019 | Tischendorf ......... A61N 5/0601 |
| 10,413,747 | B2 * | 9/2019 | Nielsen ................ G02B 6/0008 |
| 2005/0070987 | A1 * | 3/2005 | Erickson .................. A61N 1/05 607/122 |
| 2008/0077190 | A1 | 3/2008 | Kane et al. |
| 2008/0177167 | A1 | 7/2008 | Janzig et al. |
| 2008/0208278 | A1 | 8/2008 | Janzig |
| 2010/0174329 | A1 | 7/2010 | Dadd et al. |
| 2010/0230392 | A1 | 9/2010 | Robinson et al. |
| 2011/0125077 | A1 | 5/2011 | Denison et al. |
| 2011/0125078 | A1 | 5/2011 | Denison et al. |
| 2013/0030353 | A1 | 1/2013 | Seymour et al. |
| 2013/0035733 | A1 | 2/2013 | Breyen |
| 2014/0330341 | A1 | 11/2014 | Wolf, II |

OTHER PUBLICATIONS

PCT Patent Application No. PCT/US2015/027228, filed Apr. 23, 2015; International Search Report / Written Opinion; dated Jul. 24, 2015; 11 pages.

PCT Patent Application No. PCT/US2015/027231, filed Apr. 23, 2015; Invitation to Pay Additional Fees; issued Aug. 4, 2015; 5 pages.

PCT Patent Application No. PCT/US2015/027231, filed Apr. 23, 2015; International Search Report / Written Opinion; dated Oct. 16, 2015; 13 pages.

Final Rejection, U.S. Appl. No. 14/694,095, dated Dec. 8, 2017.

Campagnola, et at., "Fiber-coupled light-emitting diode for localized photostimulation of neurons expressing channelrhodopsin-2", 2008, *Journal of Neuroscience Methods*, 169:27-33.

Lademann et al., "Triggered release of model drug from AuNP-doped BSA nanocarriers in hair follicles using IRA radiation," *Acta Biomaterialia* 30, 2016; 388-396.

* cited by examiner

IMPLANTABLE DEVICE WITH OPTICAL LEAD

CROSS REFERENCE

This application is a continuation application of U.S. patent application Ser. No. 14/694,134, filed Apr. 23, 2015, which claims the benefit of U.S. Provisional Application Ser. No. 61/984,341, filed Apr. 25, 2014, which are incorporated by reference herein.

BACKGROUND

An implantable active medical devices (IMDs), also known as "active implantable medical device" (AIMD) can be equipped with bioactuator systems capable of providing light therapy or biosensor systems capable of monitoring optical characteristics (e.g., changes in refractive index or reflectivity) indicative of physiological conditions (e.g., temperature, pressure, blood oxygen content, rate of chemical processing, etc.). An IMD may be equipped with, for example, a fiber-linked optical interferometric system capable of monitoring hydrostatic pressure at a chosen site within a patient's body; e.g., blood pressure within an artery. In such a system, the proximal end of a flexible, elongated catheter is coupled to an IMD and the distal end of the catheter is positioned adjacent the site to be optically monitored. The catheter carries an optical fiber, which is optically coupled to a transceiver disposed within the IMD's canister. The transceiver directs outgoing light signals into the proximal end of the fiber, which propagate through the optical fiber until they reach the fiber's distal end. The light signals are then modulated by the body fluid (e.g., blood) being monitored and are reflected back into the fiber. The modulated signals propagate through the optical fiber once again and are received by the transceiver at the fiber's proximal end. The transceiver analyzes characteristics (e.g., amplitude in an interferometer) of the returning signals, and control circuitry coupled to the transceiver determines the blood pressure at the distal end of the catheter.

An optical feedthrough is utilized to guide the optical fiber through the canister of the IMD. The feedthrough may include a ferrule (e.g., titanium) having an aperture there, through which the optical fiber passes. To protect the circuitry of the IMD and to secure the optical fiber within the ferrule, a hermetic seal is formed between an inner surface of the ferrule and an outer surface of the optic fiber. The hermetic seal can be formed by way of a co-firing or brazing process. For example, a window-ferrule braze may be formed by threading an annular ceramic or metal (e.g., gold) preform over the window and positioning the preform against an inner shelf provided within the ferrule. If a matched seal is to be formed, the components are chosen to have similar coefficients of thermal expansion, and an inner surface of the ferrule may be metalized prior to insertion of the preform. Then, the feedthrough assembly is heated in a furnace (e.g., to over 700 degrees Celsius for approximately 10-15 minutes) to cause the brazing compound to wet the glass and flow against the ferrule to form a seal. An annealing step is then performed, and the feedthrough assembly is allowed to cool to room temperature.

BRIEF SUMMARY

The present disclosure relates to an implantable medical device with an optical lead. In particular the present disclosure relates to an implantable medical device having an optical lead and a solid state lighting device at a distal end portion of the optical lead. The solid state light source is disposed within a light transmissive ring forming a portion of a hermetic cavity and the distal end of the lead.

In one illustrative embodiment, an implantable active medical device system includes an active medical device and a lead extending between a proximal portion electrically coupled to the active medical device and a distal end portion configured to emit light. The distal end portion includes a solid state light source disposed within a light transmissive ring element.

The light transmissive ring element forms an exterior segment of the distal end portion. The light transmissive ring element defines at least a portion of a hermetic cavity.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
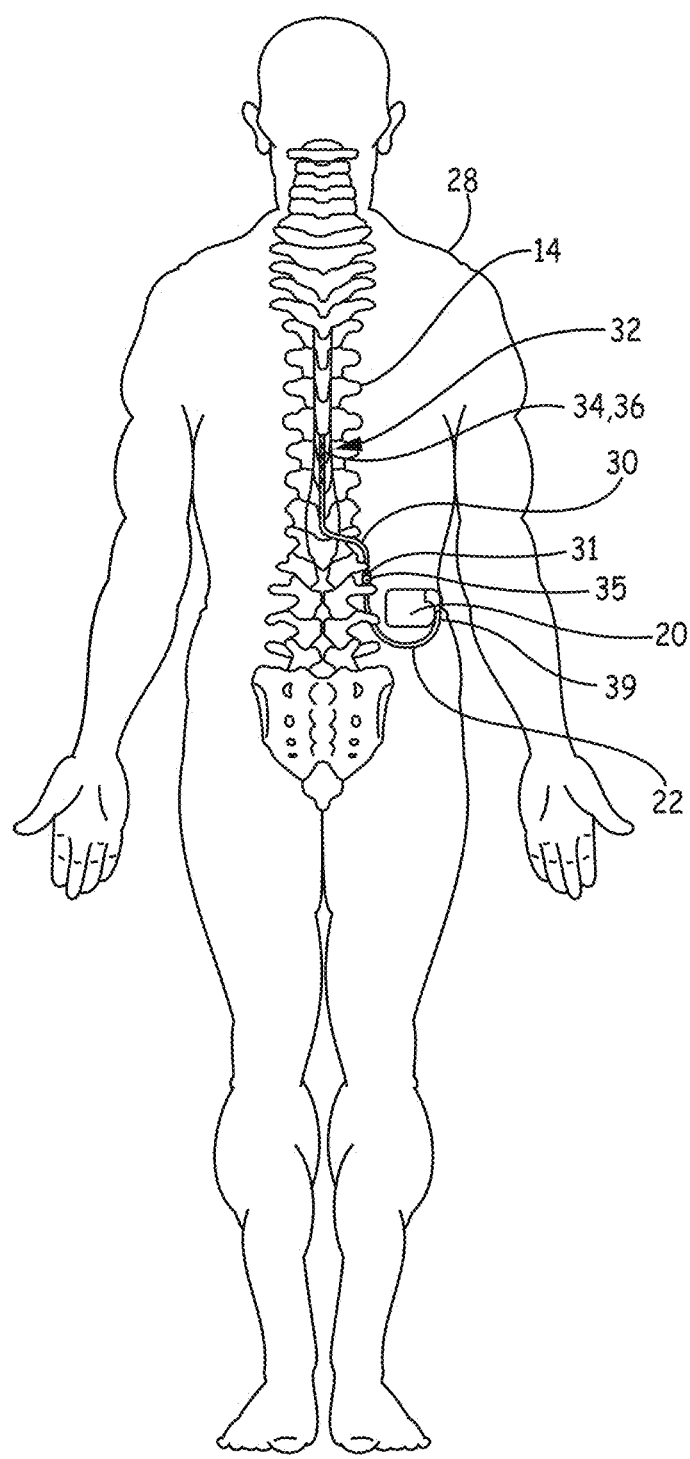
FIG. 1 is a schematic diagram of an active medical device implanted within a human body.

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "top", "bottom", "front", "rear", "lower", "upper", "beneath", "below", "above", and "on top", if used herein, are utilized for ease of description to describe spatial relationships of an element(s) to another. Such spatially related terms encompass different orientations of the device in use or operation in addition to the particular orientations depicted in the figures and described herein. For example, if an element depicted in the figures is turned over or flipped over, portions previously described as below or beneath other elements would then be above those other elements.

As used herein, when an element, component or layer is described as being "on", "connected to", "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as begin "directly on", "directly connected to", "directly coupled with" or "directly in contact with" another element, there are no intervening elements, components or layers for example.

The present disclosure relates to an implantable medical device with an optical lead. In particular the present disclosure relates to an implantable medical device having an optical lead and a solid state lighting device at a distal end portion of the optical lead. The solid state light source is disposed within a light transmissive ring forming a portion of the distal end of the lead.

A lead connector portion of a lead can mate with the lead connector receptacle and electrically couple the lead connector receptacle to provide both light and electrical sensing and/or therapy to a distal end of the lead. While the present disclosure is not so limited, an appreciation of various aspects of the disclosure will be gained through a discussion of the examples provided below.

The implantable medical device and system described herein can perform optical stimulation techniques, such as optogenetic stimulation techniques and optionally electrical sensing and/or stimulation sequentially or simultaneously. The techniques may be capable of exciting or inhibiting neural activity in target neuron populations. For optogenetic stimulation, the target neurons may be selectively transfected with genes that express opsins that are activated by light emitted into the target tissue. The light may be selected to activate an opsin to initiate neuronal spikes or to deactivate or inhibit an opsin to cease or prevent neuronal spikes. The light may also be selected to activate an opsin to suppress a neuronal spike. An optogenetic stimulation system may be configured as an implantable medical device that can deliver optical stimulation through implantable optical fibers or other light-delivery apparatus to a target tissue, such as to specific or highly specific neuron populations. The high degree of specificity provided by the optical stimulation may limit or prevent stimulation of non-target tissue, possibly reducing side effects of stimulation.

Optical stimulation of the target tissue may be configured to cause optogenetic modulation of a selected target population of cells, such as, for example, a particular area of neurons within the brain or spinal cord or nervous system or cardiac system in general. The optogenetic modulation may activate light-sensitive channel proteins, referred to herein as "opsins," that are expressed within the target population of cells. Opsin expression may be triggered by a biological vector that introduces the opsin to the target neurons. In one example, the biological vector comprises a gene therapy agent, such as a lentivirus or retrovirus that is designed to selectively transfect a particular population of neurons to selectively deliver the genes to the target neurons that will express for the desired opsins. Optogenetic modulation may be particularly useful because the genetic modification provided by biological vectors allows a specific cell population to be targeted and transfected, without modifying neighboring cell populations so that when the area is exposed to stimulation light, only the selected and transfected cell population is actually stimulated. Thus, biological vectors, such as lentiviral-based or retroviral-based vectors, provide for delivery of their genes, allowing for direct cellular targeting through genetic mechanisms as opposed to reliance on electrode positioning. This allows the "placement" of the therapeutic stimulation to be performed by a highly selective biological vector rather than relying on a surgeon who, no matter how skilled, cannot place an electrode with the same precision.

As non-limiting examples, the optical stimulation may be delivered to target tissue within the brain or spinal cord of a human patient. However, the disclosure is not so limited. Rather, optical stimulation with optional electrical sensing and/or stimulation may be delivered to any of a variety of target tissue sites to support any of a variety or therapies. A few examples include, without limitation, cardiac tissue to support cardiac therapy such as pacing, cardioversion, defibrillation, resynchronization, or other therapies, gastrointestinal tissue to support gastrointestinal therapy such as therapy to address obesity, motility disorders (e.g., gastroparesis), dyspepsia, or other therapies, pelvic floor tissue (e.g., sacral or pudendal nerve tissue) to support pelvic floor therapy such as pain therapy, urinary or fecal incontinence therapy, sexual dysfunction, or other therapies, or cranial tissue to support cranial nerve therapy such as therapy to relieve occipital neuralgia, trigeminal neuralgia, facial pain, migraine headaches, or the like.

The optogenetic system may be fully implantable in the patient. In other examples, some portions of the optogenetic stimulation system may be implantable in the patient, while other components are configured to be external to the patient. For example, one or more programmers may be external to the patient, and communicate with an implanted stimulation device via wireless telemetry. In other cases, a stimulation generator may be external to the body, and be configured to deliver electricity, light, receive sensed signals, and/or deliver fluid via percutaneously implanted optical delivery elements (such as optical fibers), leads and/or conduits. Optical fibers are described for purposes of illustration, but without limitation. In some cases, optical fibers, and electrical leads may be constructed as separate elements, or two or more of such components combined with one another in a lead or other elongated element.

The terms "light" or "optical light" as used herein refer to electromagnetic radiation having a wavelength and intensity that has a physiologically measurable effect and may include visible light, infrared light, and ultraviolet light. In some examples, light that may be used to provide the optical stimulation of system may include visible light having a wavelength of between about 380 nm and about 750 nm, infrared light having a wavelength of between about 700 nm and about 300 μm, and ultraviolet light having a wavelength between about 10 nm and about 400 nm. For example, a first optical fiber may deliver visible light having a certain wavelength and intensity, and a second optical fiber may deliver visible light having the same wavelength and intensity, or a different wavelength at the same intensity, or the same wavelength and a different intensity, or the second optical fiber may deliver non-visible light, such as infrared or ultraviolet light. The one or more optical fibers and may be coupled to the same light source or different light sources. In some cases, a single light source may be optically multiplexed across the plurality of fibers to deliver light via the different fibers at different times or to different light emissive elements on the lead.

Stereotactic or other positioning techniques may be used to precisely position the optical fibers with respect to target tissue sites. The optical stimulation may be in the form of optical light of a particular wavelength and may be delivered as pulses, e.g., with a defined pulse width and pulse rate, or a sine-wave or other light emission transmission pattern or form. Various parameters of the pulses may be defined by a stimulation program. The optical and/or electrical pulses may be independently delivered substantially continuously for a relatively long period of time, such as several seconds or more, or in pulse bursts, segments, or patterns, and may be delivered alone or in combination with pulses defined by one or more other stimulation programs.

Figure 2:
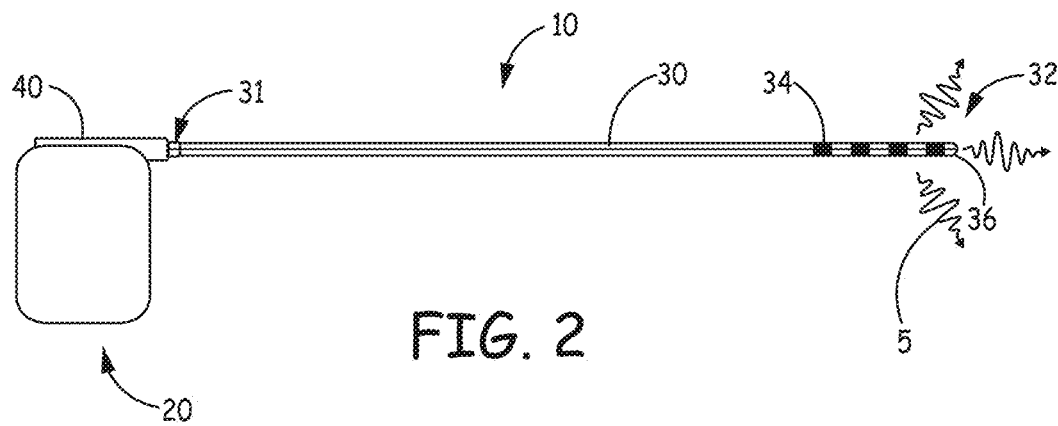
FIG. 2 is a schematic diagram of an active medical device system.
Figure 3A:
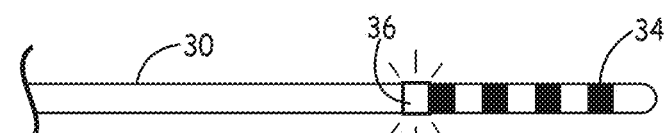
FIG. 3A-3E are side elevation views of illustrative lead distal ends illuminating light emission segments.
Figure 3B:
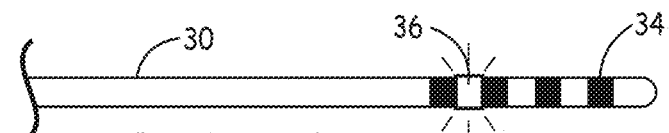
Figure 3C:
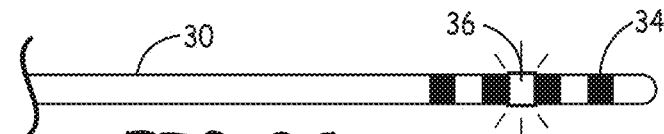
Figure 3D:
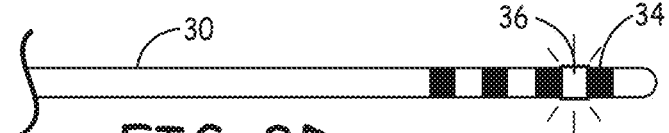
Figure 3E:
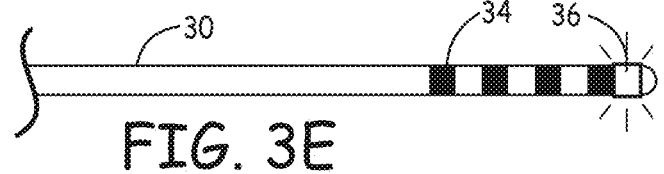

FIG. 1 is a schematic diagram of an active medical device 20 implanted within a human body of patient 28. FIG. 2 is a schematic diagram of an active medical device system 10 showing light 5 being emitted from a distal end 32 of the lead 30. The implanted active medical device 20 is illustrated as a neurostimulator, however, the implanted active medical device 20 can be any "active implantable medical device" or "implantable signal generator" as described above and can be placed in any location within a body cavity or tissue within the body, or on the surface of a patient's skin, as desired. This device can provide both electrical stimulation or sensing and optical stimulation therapy or optical stimulation therapy only.

The active medical device 20 includes a housing defining a hermetic cavity. A hybrid or electronics and a power source or battery are located within the hermetic cavity. The electronics generally control the active medical device. In some embodiments, the electronics includes memory. The memory can be any magnetic, electronic, or optical media, such as random access memory (RAM), read-only memory (ROM), electronically-erasable programmable ROM, flash memory, or the like. The power source can have a number of different sizes or capacities or configurations as required by different optical and/or electrical therapy indications. The power source can be electrically connected to the electronics and solid state light source via lead conductors extending along the length of the lead body 30. The power source can be any useful battery or inductive coil.

The active medical device 20 can be coupled to a lead extension 22 having a proximal end 39 coupled to the active medical device 20, and a lead 30 having a proximal end 31 coupled to a distal end 35 of the lead extension 22 and a distal end 32 of the lead 30 coupled to one or more electrodes 34 and/or optical windows or light emissive segments 36 emitting light 5. In other embodiments, the lead 30 proximal end 31 defines a lead connector and is coupled to a lead connector receptacle 40 of the active medical device 20, without a need for a lead extension 22. The active medical device 20 can be implanted in any useful region of the body such as in the abdomen of a patient 28, and the lead 30 is shown placed somewhere along the spinal cord 14 or in the upper body for brain stimulation.

These implantable medical device systems can also include a physician programmer and a patient programmer (not shown). The active medical device 20 can be considered to be an implantable signal generator of the type available from Medtronic, Inc. and capable of generating one or more optical and/or electrical signals occurring either simultaneously or one signal shifting in time with respect to the other, and having independently varying amplitudes and signal widths. The active medical device 20 contains a power source and the electronics for sending precise, electrical and/or optical signals to the patient to provide the desired treatment therapy.

FIGS. 3A-3E are side elevation views of illustrative lead 30 distal ends illuminating light emission segments 36. These figures illustrate the selective illumination or light emission from one of the five individual light emission segments 36. The light emission segments 36 are separated by electrode 34 segments. There are five individual light emission segments 36 separated by four electrode 34 segments. Light can be selectively emitted from one or more of the individual light emission segments 36, as described below. Electricity can be selectively provided to one or more of the individual electrode 34 segments.

The individual light emission segments 36 can be formed of any useful light transmissive material such as a glass or sapphire. The light emission segments 36 are preferably in the form of a ring or annular ring of light transmissive material.

Figure 4:
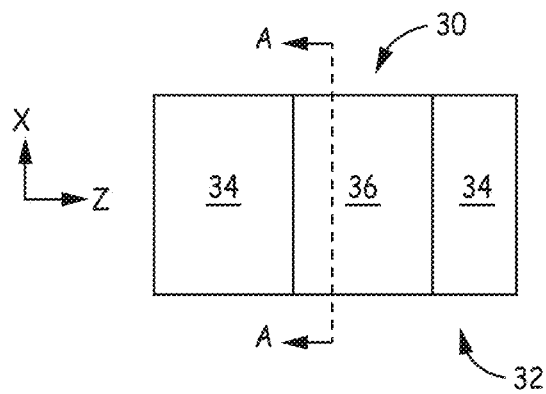
FIG. 4 is a schematic diagram side elevation of a portion of an illustrative lead distal end.
Figure 5:
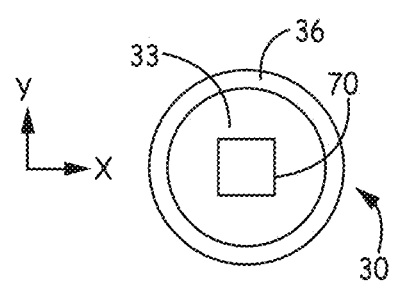
FIG. 5 is a schematic cross-sectional view of an illustrative single solid state light source embodiment of FIG. 4 taken along line A-A.
Figure 6:
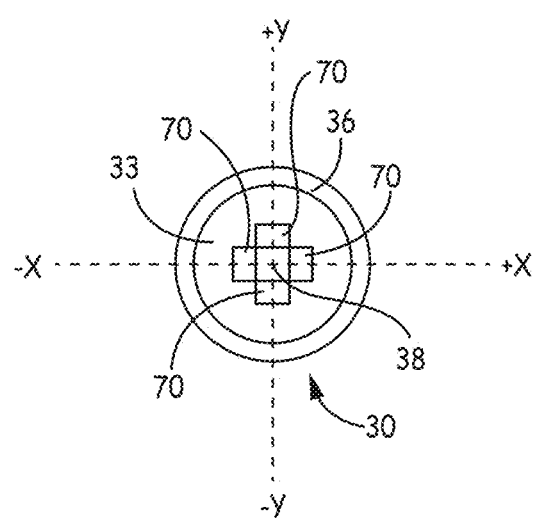
FIG. 6 is a schematic cross-sectional view of an illustrative multiple solid state light source embodiment of FIG. 4 taken along line A-A.
Figure 7:
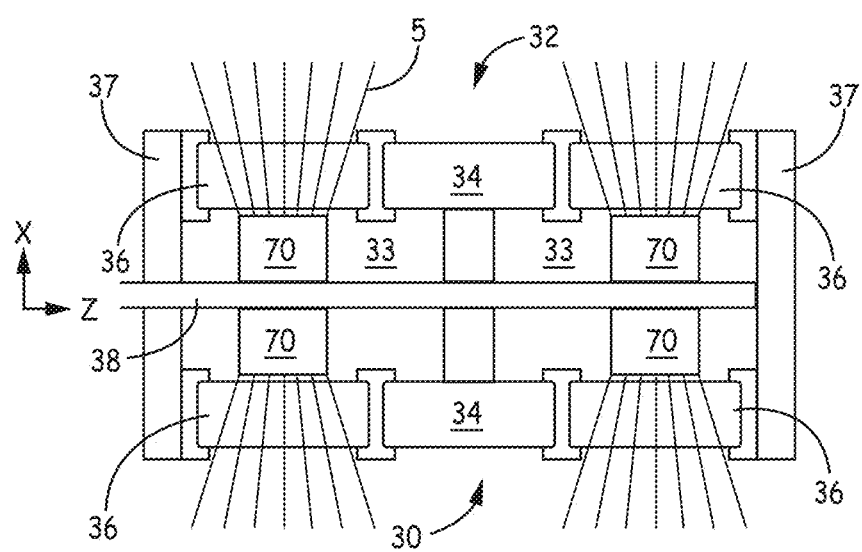
FIG. 7 is a schematic cross-sectional view of an illustrative multiple solid state light source embodiment taken along a longitudinal axis of FIG. 4.

FIG. 4 is a schematic diagram side elevation of a portion of an illustrative lead distal 30 end 32. FIG. 5 is a schematic cross-sectional view of an illustrative single solid state light source embodiment of FIG. 4 taken along line A-A. FIG. 6 is a schematic cross-sectional view of an illustrative multiple solid state light source embodiment of FIG. 4 taken along line A-A. FIG. 7 is a schematic cross-sectional view of an illustrative multiple solid state light source embodiment taken along a longitudinal axis of FIG. 4. An x-y axis or x-z axis is illustrated on each figure to aid in orientation of the illustrated view.

The distal end portion 32 includes a solid state light source 70 disposed within a light transmissive ring element 36. The light transmissive ring element 36 forming an exterior segment of the distal end portion 32. The light transmissive ring element 36 defines at least a portion of a hermetic cavity 33. The light transmissive ring element 36 can be hermetically sealed via brazing or diffusion bonding to the distal end 32 elements such as the electrode 34 segments.

The solid state light source 70 can be any useful solids state light element. Solid state light elements include light emitting diodes (LEDs), organic light emitting diodes (OLEDs), laser diodes, vertical cavity surface emitting lasers (VCSELs) and polymer light emitting diodes, for example. In some embodiments the solid state light source 70 is optically coupled to the light transmissive ring element 36 to transmit light from the hermetic enclosure 33 and through the light transmissive ring element 36 and emit light into the environment surrounding the lead 30. In some of these embodiments an optically coupling fluid fills open space in the hermetic cavity 33 and substantially matches the index of refraction of the light transmissive ring element 36 and/or the solid state light source 70. In other embodiments the solid state light source 70 is spaced apart from the light transmissive ring element 36 by an air gap.

The light transmissive ring element 36 can be hermetically bonded to an electrode 34 that can be described as an electrode ring element 34. The electrode ring element 34 forms an exterior segment of the distal end portion 32. In many embodiments the hermetic cavity 33 is further defined by an end cap 37 hermetically bonded to the electrode ring element 34 or light transmissive ring element 36. The end cap 37 can be formed of any useful metal or light transmissive material, as described herein.

The electrode ring element 34 can be formed of any useful electrically conductive material and also form a hermetic barrier. In many embodiments, the electrically conducting contact rings are formed of a metallic material such as, for example, titanium, stainless steel, MP35N, niobium, tantalum, platinum, and alloys or combinations thereof. In some embodiments, the electrode ring element 34 is formed of a metallic material such as, for example, titanium.

The element(s) and/or compounds used to form the light transmissive ring element 36 are selected in a manner to reduce tensile stresses with electrode ring elements 34. For example, light transmissive ring element 36, employing glass, has a coefficient of thermal expansion (CTE) value about equivalent to or within 15% of the CTE associated with, electrode ring element 34.

In many embodiments the lead distal end portion 32 includes a plurality of solid state light sources 70 and a plurality of light transmissive ring elements 36. In many of these embodiments, each light transmissive ring element 36 surrounds one of the solid state light sources 70 forming a transmissive ring and light source pair. Each transmissive ring and light source pair is spaced apart for an adjacent transmissive ring and light source pair by an electrode ring element 34. The lead distal end portion 32 can include a plurality of transmissive ring and light source pairs and each transmissive ring and light source pair is activated independently of each other. FIG. 5 and FIG. 6 illustrate a transmissive ring and light source pair.

In FIG. 5 a single light source 70 is disposed within the hermetic cavity at least partially defined by the light transmissive ring element 36. Only one or a single solid state light source 70 is disposed within a single light transmissive ring element 36 and the single solid state light source 70 emits light through an entire circumference of the single light transmissive ring element 36. The single solid state light source 70 transmits 360 degrees of light through the light transmissive ring element 36.

In FIG. 6 a plurality or four light sources 70 are disposed within the hermetic cavity at least partially defined by the light transmissive ring element 36. Four solid state light sources 70 are disposed within a single light transmissive ring element 36 and the four solid state light sources 70 combine to emit light through an entire circumference of the single light transmissive ring element 36. The four solid state light sources 70 transmit 360 degrees of light through the light transmissive ring element 36. The four solid state light sources 70 are electrically coupled to an electronics element 38 that can include an integrated circuit or is electrically coupled to electronics or a circuit. The solid state light sources 70 can emit light primarily in different directions, such as a −x or +x or −y or +y directions. The solid state light sources 70 can be configured to be activated independently of each other. Thus, one solid state light source 70 can be activated that emits light primarily in the +x direction while one or more of the remaining solid state light sources 70 remains non-activated, or one solid state light source 70 can be activated that emits light primarily in the −x direction while one or more of the remaining solid state light sources 70 remains non-activated, or one solid state light source 70 can be activated that emits light primarily in the −y direction while one or more of the remaining solid state light sources 70 remains non-activated, or one solid state light source 70 can be activated that emits light primarily in the +y direction while one or more of the remaining solid state light sources 70 remains non-activated.

In FIG. 7 a plurality or two light sources 70 are disposed within the hermetic cavity at least partially defined by the light transmissive ring element 36. Two solid state light sources 70 are disposed in opposing directions and within a single light transmissive ring element 36 and the two solid state light sources 70 combine to emit light through an entire circumference of the single light transmissive ring element 36. The two solid state light sources 70 transmit 360 degrees of light through the light transmissive ring element 36. The two solid state light sources 70 are electrically coupled to an electronics element 38 that can include an integrated circuit or is electrically coupled to electronics or a circuit. The solid state light sources 70 can emit light primarily in different directions or opposing directions, such as a −x or +x directions. The solid state light sources 70 can be configured to be activated independently of each other. Thus, one solid state light source 70 can be activated that emits light primarily in the +x direction while remaining solid state light sources 70 remain non-activated, or one solid state light source 70 can be activated that emits light primarily in the −x direction while the remaining solid state light source 70 remains non-activated.

In some embodiments, the plurality of solid state light sources 70 is an array of at least ten solid state light sources 70. The array of at least ten solid state light sources 70 can be arranged on an annular element and co-axially disposed within the single light transmissive ring element 36.

Thus, embodiments of the IMPLANTABLE DEVICE WITH OPTICAL LEAD are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. An implantable active medical device system comprising:
    an active medical device;
    a lead extending between a proximal portion electrically coupled to the active medical device and a distal end portion configured to emit light, the distal end portion comprising:
        a solid state light source disposed within a light transmissive ring element, the light transmissive ring element forming an exterior segment of the distal end portion, the light transmissive ring element defining at least a portion of a hermetic cavity; and
    an optically coupling fluid that fills open space in the hermetic cavity wherein the optically coupling fluid substantially matches the index of refraction of the light transmissive ring element.

2. The implantable active medical device system according to claim 1 wherein the hermetic cavity is further defined by an end cap hermetically bonded to the light transmissive ring element.

3. The implantable active medical device system according to claim 1 wherein a plurality of solid state light sources are disposed within a single light transmissive ring element.

4. The implantable active medical device system according to claim 3 wherein each of the plurality of solid state light sources is activated independently of each other.

5. The implantable active medical device system according to claim 3 wherein the plurality of solid state light sources comprise two solid state light sources directing light in opposing directions.

6. The implantable active medical device system according to claim 3 wherein the plurality of solid state light sources comprise four solid state light sources directing light in four different directions.

7. The implantable active medical device system according to claim 3 wherein the plurality of solid state light sources comprise an array of at least ten solid state light sources.

8. The implantable active medical device system according to claim 1 wherein only one solid state light source is disposed within a single light transmissive ring element and the single solid state light source emits light through an entire circumference of the single light transmissive ring element.

9. The implantable active medical device system according to claim 1 wherein the solid state light source emits light through an entire circumference of the light transmissive ring element.

10. The implantable active medical device system according to claim 1 wherein the solid state light source is a light emitting diode.

11. The implantable active medical device system according to claim 1 wherein the light transmissive ring element consists of sapphire.

12. The implantable active medical device system according to claim 1 wherein the solid state light source is completely disposed within the hermetic cavity.

13. The implantable active medical device system according to claim 1 further comprising one or more optical fibers coupled to the solid state light source.

14. The implantable active medical device system according to claim 1 further comprising a plurality of optical fibers coupled to the solid state light source.

15. The implantable active medical device system according to claim 14 wherein the solid state light source is multiplexed across the plurality of optical fibers to selectively deliver light via the different fibers.

16. The implantable active medical device system according to claim 1 wherein the solid state light source transmits 360 degrees of light through the light transmissive ring element.

17. The implantable active medical device system according to claim 1 wherein the transmissive ring element comprises sapphire.

* * * * *